United States Patent [19]

Cooray

[11] Patent Number: 4,546,136

[45] Date of Patent: Oct. 8, 1985

[54] ORGANOTIN-CONTAINING COMPOSITION FOR THE STABILIZATION OF POLYMERS OF VINYL CHLORIDE

[75] Inventor: Boyd Cooray, Oldham, England

[73] Assignee: Akzo N.V., Arnhem, Netherlands

[21] Appl. No.: 611,523

[22] Filed: May 17, 1984

[30] Foreign Application Priority Data

May 18, 1984 [NL] Netherlands ............... 8301760

[51] Int. Cl.$^4$ .................. C08K 5/58; C07F 7/22
[52] U.S. Cl. ......................... 524/180; 556/105
[58] Field of Search ............... 524/180, 182; 260/429.7

[56] References Cited

U.S. PATENT DOCUMENTS

| Re. 30,810 | 12/1981 | Kugele et al. | 524/182 |
| 2,731,440 | 1/1956 | Stefl et al. | 524/182 |
| 3,525,760 | 8/1970 | Seki et al. | 524/180 |
| 3,525,761 | 8/1970 | Seki et al. | 524/180 |
| 3,979,359 | 9/1976 | Kugele et al. | 524/182 |
| 4,111,903 | 9/1978 | Hoch et al. | 524/180 |

Primary Examiner—Veronica P. Hoke
Attorney, Agent, or Firm—Parkhurst & Oliff

[57] ABSTRACT

An organotin-containing composition for the stabilization of polymers or copolymers of vinyl chloride in which there is incorporated a stabilizing amount of an organotin compound containing at least two tin atoms and which is a mercapto, hydroxy or alkoxy substituted ester of a mercapto acid substituted organotin mercapto acid diester.

13 Claims, No Drawings

ORGANOTIN-CONTAINING COMPOSITION FOR THE STABILIZATION OF POLYMERS OF VINYL CHLORIDE

The invention relates to an organotin-containing composition for the stabilization of polymers or copolymers of vinyl chloride in which there is incorporated a stabilizing amount of an organotin compound containing at least two tin atoms, to a process for the preparation of such a composition, to polymers or copolymers of vinyl chloride in which there is incorporated a stabilizing amount of said composition, and to shaped objects entirely or partly made from these stabilized polymers.

A composition of the type indicated above is disclosed in U.S. Pat. No. 4,111,903. The organotin compound, which contains at least two tin atoms, is prepared by reacting one mole of an alkylene glycol dimercaptoacetate with two moles of an organotin oxide or an organotin dihalide and two moles of an alkyl ester of a mercapto carboxylic acid, an alkyl mercaptan, and/or a monoalkyl maleate. It has been found that the stabilizing effect of such a composition can be considerably increased or the amount in which it is to be incorporated in order to obtain a particular stabilizing effect be considerably reduced by the incorporation in said composition of an organotin compound which corresponds to the formula:

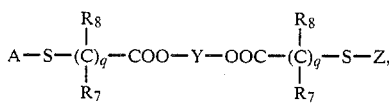

wherein A and Z represent tin-containing groups which may be the same or different and both correspond to the formula:

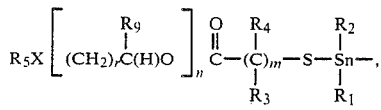

wherein $R_1$ and $R_2$ may be the same or different and may represent an alkyl group having 1 to 18 carbon atoms, the group

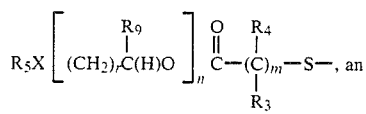

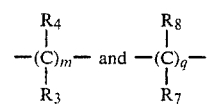  group or the group

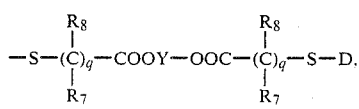

wherein D corresponds to the same formula as A and Z, with the proviso that when in the group A $R_1$ and $R_2$ both represent an alkyl group or the group

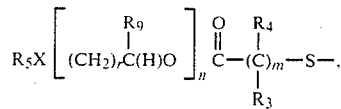

$R_1$ in the group Z and/or D represents an alkyl group and $R_2$ the group

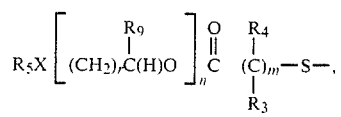

or $R_1$ and/or $R_2$ in the group Z and/or D represent the group

wherein $R_6$ represents an alkyl group having 1 to 18 carbon atoms which may be substituted or not with an alkoxy group having 1 to 18 carbon atoms, a polyoxyalkylene group consisting of oxyalkylene groups having 1 to 4 carbon atoms and of which the end group is an alkyl group or a hydrogen atom, a cycloalkyl group having 3 to 6 carbon atoms, an alkenyl group having 2 to 4 carbon atoms or a phenyl group;

$R_3$, $R_4$, $R_7$ and $R_8$ may be the same or different and have the meaning of a hydrogen atom, an alkyl group having 1 to 18 carbon atoms or an aryl group;

$R_5$ represents a hydrogen atom, an alkyl group having 1 to 18 carbon atoms, a cycloalkyl group having 3 to 6 carbon atoms or a substituted or unsubstituted aryl group; $R_9$ has a meaning of a hydrogen atom or a methyl group;

X represents an O or S atom;

Y has the meaning of a divalent, substituted or unsubstituted aliphatic, cycloaliphatic or aromatic group having not more than 20 carbon atoms; and m and q have the meaning of a whole number from 1 to 6, n and r a whole number from 1 to 3 and p represents a whole number from 1 to 12.

For ease of preparation preference is given to a composition in which A, Z and D in the above formulae are identical.

It has been found that generally very favourable results are obtained when in the above formula for the organotin compound the groups $$-\overset{R_4}{\underset{R_3}{(C)_m}}- \text{ and } -\overset{R_8}{\underset{R_7}{(C)_q}}-$$

represent a branched or non-branched alkylene group having 1 to 6 carbon atoms, and Y is a branched or non-branched alkylene group or alkylene oxyalkylene group having 2 to 10 carbon atoms. Preference is given to an organotin compound in which the groups

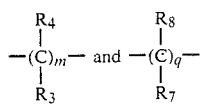

each represent a methylene group or ethylene group, Y is an ethylene group or butylene group, n=1 and $R_5$ represents an alkyl group having 1 to 8 carbon atoms.

It has further been found that when in the first-mentioned formula $R_1$ represents an alkyl group having 1 to 18 carbon atoms and $R_2$ represents the group

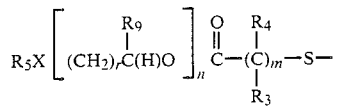

an organotin composition having a remarkably high stabilizer performance is obtained when it contains a synergistic amount of a compound of the first-mentioned formula wherein $R_1$ and $R_2$ may be the same or different and represent an alkyl group having 1 to 18 carbon atoms. It has been found that this synergistic effect occurs when the weight ratio between the amount of monoalkyltin compound and dialkyltin compound is at least 1:20.

It has further been found that a synergistic effect is also obtained when the organotin-containing composition contains 5 to 90% by weight of an organotin compound of the first-mentioned formula and 10 to 95% by weight of a compound of the formula

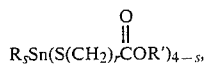

wherein R represents an alkyl group having 8 to 18 carbon atoms, R' is an alkyl group having 1 to 18 carbon atoms or an aryl group, r is an integer from 1 to 6 and s=1 or 2.

Examples of at least two tin atoms-containing organotin compounds according to the invention are: bis(di 2-n-butoxycarbonyl ethyl tin 2-butoxyethylthioglycolate)ethylene glycol dithioglycolate, bis(di 2-n-butoxycarbonylethyl tin 2-ethylthioethylthioglycolate)ethylene glycol dithioglycolate, bis(butyltin dibutoxyethylthioglycolate)propanediol-1,3 dithioglycolate, bis(di 2-n-butoxycarbonylethyl tin 2-hexoxyethylthiopropionate)butanediol-1,4 dithiopropionate, bis(2-ethylhexyltin dipropoxyethylithioglycolate)hexanediol-1,6 dithioglycolate, bis(butyltin di-2-n-butoxyethylthioglycolate)propanediol-1,3 dithiopropionate.

An important advantage to the organotin-containing compositions according to the invention is that even if they contain only a small percentage (say, 15% by weight) of an organotin compound of the first-mentioned formula, the same stabilizing efficiency as that of the known organotin-containing compositions may be obtained when the proportion of tin in the polymer is reduced by for instance 10% by weight, which means a considerable economy.

The invention also relates to a process for the preparation of an organotin-containing composition as described in the afore-mentioned U.S. Pat. No. 4,111,903, where an organotin oxide or an organotin halide is reacted with the esterification products of a mercapto-substituted carboxylic acid and a monofunctional and a bifunctional alcohol.

The process according to the invention is characterized in that (A) the organotin compound is an alkyltin compound having a branched or non-branched alkyl group containing 1 to 18 carbon atoms, the monoalkyltin compound forming at least 5% by weight of the alkyltin compound, and/or an estertin compound of the formula

for the ester group, wherein $R_6$ has the afore-mentioned meaning;

(B) the mercapto-substituted carboxylic acid is a compound of the formula

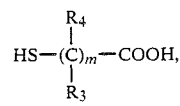

wherein $R_3$, $R_4$ and m have the afore-mentioned meaning;

(C) the monofunctional alcohol is a compound with corresponds to the formula

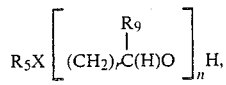

wherein $R_5$, $R_9$, X, r and n have the aforementioned meaning;

(D) the divalent alcohol is a compound which corresponds to the formula HO—Y—OH, wherein Y has the afore-mentioned meaning, and (E) the molar ratio between the bifunctional alcohol and the monofunctional alcohol is in the range of 1:9 to 9:1.

Examples of compounds which correspond to the formula

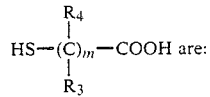

4-mercaptobutyric acid
5-mercaptopentanoic acid
6-mercaptohexanoic acid
7-mercaptoheptanoic acid
2-mercaptopropionic acid
orthomethyl mercaptobenzoic acid
2-mercapto-2,2-dimethylacetic acid
2-mercapto-2-butylacetic acid
2-mercapto-2-benzylacetic acid
3-mercapto-2-methyl-propionic acid.

Preference is given to 2-mercaptopropionic acid and especially to mercapto acetic acid and 3-mercaptopropionic acid.

Examples of compounds which correspond to the formula

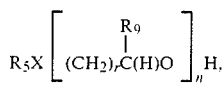

are:
2-octyloxyethanol
2-decyloxyethanol
2-tetradecyloxyethanol
2-(2-n-octyloxyethoxy)ethanol
2-(2-n-octadecyloxyethoxy)ethanol
2-(butylthio)ethanol
2-(octylthio)ethanol
2-(octadecylthio)ethanol
2-(butylthio)-1-methylethanol
2-(dodecylthio)-1-methylethanol
2-(2-chloroethoxy)ethanol
4-ethoxy-3-methoxy benzyl alcohol
Preference is given to
1-ethylthio-2-propanol
2-(2-ethoxyethoxy)ethanol
1-methoxy-2-propanol
2-(2-methoxyethoxy)ethanol
tripropylene glycol monomethyl ether, whereas optimum results have been obtained with
2-butoxyethanol
2-ethoxyethanol
2-methoxyethanol
2-(2-n-butoxyethoxy)ethanol
2-(ethylthio)ethanol
1-ethoxy-2-propanol
2-(methoxymethoxy)ethanol
3-(3-ethoxy-n-propoxy)propanol
Examples of compounds which correspond to the formula HO—Y—OH are
3-cyclohexene-1,1-dimethanol
cis-1,5-cyclooctane diol
1,3-cyclopentane diol
1,10-decane diol
1,4-butyne diol
1,5-bis(β-hydroxyethoxy)naphthalene
1,4-dihydroxy-1,2,3,4-tetrahydronaphthalene
3-chloro-1,2-propane diol
2-ethyl-2-methyl-1,3-propane diol
Preference is given to
1,3-propanediol
1,5-pentanediol
1,6-hexanediol
1,3-cyclohexanediol
1,4-cyclohexanediol
1,4-dimethylolbenzene
2,2-diethyl-1,3-propanediol
2-ethyl-1,3-hexanediol
2-methyl-2,4-pentanediol,
whereas optimum results have been obtained with
1,2-ethanediol
1,4-butanediol
1,4-cyclohexanedimethanol
1,2-cyclohexanediol
glycerol
2,2-dimethyl-1,3-propanediol
thioglycerol
bis(2-hydroxyethyl)ether
bis(3-hydroxy-n-propyl)ether
Preference is given to a process in which the molar ratio between the bifunctional alcohol and the monofunctional alcohol is in the range of 5:9 and 9:1.

It has been found that very favourable results are obtained when the monoalkyltin compound forms 10 to 20 percent by weight of the alkyltin compound.
Particularly for ease of preparation preference is given to a process in which the monofunctional alcohol used is a compound of the formula

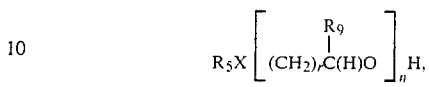

wherein the group

has the meaning of a —CH$_2$CH$_2$O— or a

group.
The process according to the invention may be carried out as follows:
One mole of ethylene glycol dithioglycolate is reacted with two moles of an organotin oxide or organotin halide and two moles of an alkoxyalkyl ester or alkylthioalkyl ester of, for instance, thioglycolic acid. The reaction is usually carried out by heating the reactants at 70° to 100° C., preferably 90° to 95° C. under subatmospheric pressure until the theoretical amount of water has been evolved. The reaction mixture is preferably sparged with an inert gas, such as nitrogen, during the heating to assist in the removal of water. The products prepared in this way can be used without purification or further treatment to stabilize polymers or copolymers of vinyl chloride.
In addition to tin compounds there may be present other heat and light stabilizers, such as salts of barium, cadmium, strontium, zinc and other polyvalent metals, organic phosphites, and polyhydric alcohols, lubricants, antioxidants, solvents, and the like.
The organotin compositions of the present invention need be incorporated in only a small amount in order that a sufficient stabilizing effect may be produced. The amount to be incorporated may be in the range of 0.2 to 5 percent by weight. As a rule, the proportion to be used will be in the range of 0.5 to 3% by weight, calculated on the vinyl chloride polymer. Optionally, other additives to be contained in the polymer may beforehand be incorporated into the stabilizer composition to be subsequently mixed with said polymer. On the other hand, the organotin-containing composition and further additives also may be incorporated separately into the polymer to be stabilized, for example during processing.
The stabilizer compositions of the present invention are particularly suitable for improving the thermal stability of any conceivable polyvinyl chloride resin, irrespective of its way of preparation; for example solution polymerization, emulsion polymerization and suspension polymerization.
The term polyvinyl chloride as used herein not only refers to any conceivable type of homopolymer of vinyl chloride, and post-chlorinated polyvinyl chloride, but also to copolymers having vinyl chloride as its major constituent, and a minor proportion of other copolymerizable monomers, such as copolymers of vinyl chloride and vinyl acetate, copolymers of vinyl chloride and vinylidene choride, compolymers of vinyl chloride and acrylonitrile, copolymers of vinyl chloride and maleic or fumaric esters and copolymers of vinyl chloride and styrene, and also mixtures containing a high proportion of polyvinyl chloride resin and a low proportion of some other synthetic resin, such as chlorinated polyethylene, copolymers of acrylonitrile, butadiene and styrene.

The invention will be further described in, but not limited by the following examples.

The stabilizer compositions according to the invention were tested at 185° C. in a rigid PVC formulation under both dynamic and static conditions. They were compared with a standard stabilizer mixture consisting of 15% by weight of monobutyl tin tri 2-ethylhexyl thioglycolate and 85% by weight of dibutyltin di 2-ethylhexyl thioglycolate. Use was made of the following test methods:

1. MILL TEST FOR ASSESSING THE BEHAVIOUR DURING PROCESSING

After gelation for 4 minutes the various constituents of each specific formulation were intermixed on a two-roll laboratory mill, the rolls both having a speed of 4 rpm. Sticking of the polymer of the rolls (stick time) and change in colour were observed. The change in colour was taken as a measure of the rate of decomposition of the PVC. In the examples the results of the experiments are rated from 1 (colourless) to 10 (black).

2. STATIC OVEN TEST

After gelation for 4 minutes the various constituents of each specific formulation were mixed on a two-roll laboratory mill at 160° C. The samples required were cut out of the approximately 1.5 mm thick sheet emerging from the mill. The thermal stability tests were carried out at 185° C. in a Heraeus oven, which was provided with rotating sample trays. The samples were removed from the oven at 10 minute intervals, after which they were visually inspected for change in colour. In the examples the test results are rated from 1 (colourless) to 10 (black), as in the mill test.

EXAMPLE I

Preparation of bis(di 2-n-butoxycarbonylethyl tin 2-butoxyethyl thioglycolate)ethylene glycol dithioglycolate In a 1-1 three-necked flask fitted with a reflux condenser 300 g (3.26 moles) of thioglycolic acid were mixed with 81 g (1.30 moles) of ethylene glycol and 76.5 g (0.65 moles) of 2-butoxyethanol. After adding 450 ml of toluene and 2.5 g of p-toluene sulphonic acid the mixture was heated with refluxing for 3½ hours, during which time 58.6 ml (3.26 moles) of water were separated in the form of an azeotrope. The thioglycolate mixture was isolated by evaporating toluene. Of this product mixture 60.8 g were reacted with 100 g of di 2-n-butoxycarbonylethyltin dichloride. After adding 250 ml of toluene the mixture was stirred and heated to 35°-40° C. and 40.8 g of sodium bicarbonate were slowly added. This was followed by the addition of 200 ml of distilled water. Stirring was continued for 2 hours at 35°-40° C. After running off the aqueous phase the product was isolated, as a light straw coloured mobile liquid, by solvent evaporation. The tin content was 18.2% by weight (theory=17.7%).

EXAMPLE II

Preparation of bis(di 2-n-butoxycarbonylethyltin 2-ethylthioethyl thioglycolate)ethylene glycol dithioglycolate Using the same procedure as given in Example I 300 g (3.26 moles) of thioglycolic acid were mixed with 81 g (1.30 moles) of ethylene glycol and 69.4 g (0.65 moles) of 2-ethylthioethanol. After adding 450 ml of toluene and 2.5 g of p-toluene sulphonic acid the mixture was heated with refluxing for 3 hours, during which time 58.6 ml (3.26 moles) of water were separated in the form of an azeotrope. The thioglycolate mixture was isolated by evaporation of toluene.

Of that mixture 61.2 g were reacted with 100 g of di 2-n-butoxycarbonylethyltin dichloride. After adding 250 ml of toluene the mixture was stirred and heated to 35° to 40° C., followed by slowly adding 40.8 g of sodium bicarbonate. Subsequently, 200 ml of distilled water were added and the mixture was stirred until after 2 hours neutral pH was reached. After running off the aqueous phase the product was isolated, as a pale yellow mobile liquid, by solvent evaporation. The tin content was 18.4% by weight.

EXAMPLE III

A flask was charged with 100 g of a mixture of 15% by weight of mono- and 85% by weight of dibutyltin chloride to which there was added a mixture of 53.0 g (0.25 moles) of ethylene glycol bisthioglycolate and 41.34 g (0.215 moles) of 2-butoxyethyl thioglycolate. To the resulting mixture there were slowly added at 40° C. 63.6 g of sodium bicarbonate together with 500 ml of distilled water. Stirring for 1 hour at 40° C. caused the pH of the aqueous layer to reach 7. After the aqueous layer had been run off, the stabilizer was isolated by removing any residual moisture through evaporation under reduced pressure (1.9 kPa).

EXAMPLE IV 104.5 (0.5 moles) of monobutyltin oxide were added gradually to a mixture of 120.5 g (0.57 moles) of ethylene glycol bisthioglycolate and 80 g (0.42 moles) of 2-butoxyethyl thioglycolate at a temperature of 80° C. with stirring until a clear solution was obtained. Subsequently, the temperature was raised to 105° C. over a period of 15 minutes. The resulting product was a clear, colourless, mobile liquid. The yield was practically quantitative.

EXAMPLE V

The following rigid PVC formulation was prepared and tested in the above-described manner:

|  | parts by weight |
|---|---|
| PVC (prepared by suspension polymerization; K-value 57) | 100 |
| glycerol mono-oleate | 0,9 |
| lignite wax marketed by Hoechst under | 0.3 |

| | |
|---|---|
| the trademark "wax E" processing aids derived from acrylic acids | 3,2 |
| stabilizer | 1,5 |

The organotin compounds used were:

| | |
|---|---|
| bis(di 2-n-butoxycarbonylethyl)tin-ethylene glycol dithioglycolate = | $(BuAc)_2Sn(EGdTG)$. |
| di 2-n-butoxycarbonylethyltin di-2-butoxyethyl-thioglycolate = | $(BuAc)_2Sn(SCH_2COCH_2CH_2OC_4H_9)_2$ |
| monobutyltin ethylene glycoldi-thioglycolate = | $BuSn(EGdTG)_{3/2}$ |
| dibutyltin ethylene glycoldi-thioglycolate = | $Bu_2Sn(EGdTG)$. |
| monobutyltin tri 2-butoxyethyl-thioglycolate = | $BuSn(SCH_2COCH_2CH_2OC_4H_9)_3$ |
| dibutyltin di-2-butoxyethyl-thioglycolate = | $Bu_2Sn(SCH_2COCH_2CH_2OC_4H_9)_2$ |
| a mixture of mono- and dibutyltin 2-ethylhexylthioglycolate derived from a mixture of 15 wt. % mono-butyltintrichloride and 85 wt. % dibutyltindichloride = | standard. |

The following table shows the results of a Mill test with the above compounds and the reaction product of Example I.

TABLE I

| | 5 | 10 | 15 | 20 | 25 | 30 | 35 | 40 |
|---|---|---|---|---|---|---|---|---|
| $(BuAc)_2Sn(EGdTG)$ | 1 | 3 | 3 | 4 | 5 | 9 | stuck | |
| $(BuAc)_2Sn(SCH_2COCH_2CH_2OC_4H_9)_2$ | 1 | 2 | 3 | 3 | 9 | stuck | | |
| standard | 1 | 2 | 3 | 5 | 6 | 7 | 9 | stuck |
| product of ex. 1 | 1 | 2 | 2 | 3 | 3 | 5 | 9 | stuck |

The colour development during the oven test is given in Table II.

TABLE II

| | Colour development during oven test at 185° C. Time (min) | | | | | | | |
|---|---|---|---|---|---|---|---|---|
| Organotin compound | 0 | 10 | 20 | 30 | 40 | 50 | 60 | 70 |
| $(BuAc)_2Sn(EGdTG)$ | 1 | 1 | 2 | 3 | 4 | 5 | 9 | |
| $(BuAc)_2Sn(SCH_2COCH_2CH_2OC_4H_9)_2$ | 1 | 2 | 3 | 5 | 7 | 9 | | |
| Standard | 1 | 1 | 2 | 3 | 4 | 5 | 6 | 7 |
| Product of ex. 1 | 1 | 1 | 1 | 1 | 2 | 3 | 4 | 7 |

The results in the above tables clearly show that at equal concentration the product of Example I displays a higher stabilizing efficiency than the products $(BuAc)_2Sn(EGdTG)$ and $(BuAc)_2Sn(SCH_2COCH_2CH_2OC_4H_9)_2$.

The product of Example II showed similar test results.

EXAMPLE VI

Tested in the same PVC formulation as used in Example V there were compared: a mixture of 15% by weight of $BuSn(EGdTG)_{3/2}$ and 85% by weight of $Bu_2Sn(EGdTG)$ 15 wt.%

$$BuSn(SCH_2COCH_2CH_2OC_4H_9)_3$$

and 85 wt.%

$$Bu_2Sn(SCH_2COCH_2CH_2OC_4H_9)_2,$$

the standard organotin composition and the reaction product of Example III according to the invention. The results of the Mill test are given in Table III. The results of the oven test are listed in Table IV.

TABLE III

| | Colour development during Mill test at 185° C. time (min) | | | | | | | |
|---|---|---|---|---|---|---|---|---|
| Organotin compound | 5 | 10 | 15 | 20 | 25 | 30 | 35 | 40 |
| 15% monobutyltin $(EGdTG)_{3/2}$ | 1 | 2 | 2 | 3 | 4 | 5 | 9 | |
| 15% monobutyltin $(SCH_2COCH_2CH_2OC_4H_9)_3$ | 1 | 2 | 2 | 3 | 5 | 5 | 9 | |
| Standard | 1 | 2 | 3 | 5 | 6 | 7 | 9 | |
| Product of ex. III | 1 | 1 | 2 | 2 | 3 | 4 | 5 | 9 |

TABLE IV

| | Oven test | | | |
|---|---|---|---|---|
| Time (min) | 15% monobutyltin $(EGdTG)_{3/2}$ | 15% monobutyltin $(SCH_2COCH_2CH_2OC_4H_9)_3$ | std. | Example III |
| 0 | 1 | 1 | 1 | 1 |
| 10 | 1 | 1 | 1 | 1 |
| 20 | 2 | 2 | 2 | 2 |
| 30 | 2 | 2 | 3 | 2 |
| 40 | 3 | 3 | 4 | 2 |
| 50 | 4 | 4 | 5 | 2 |
| 60 | 4 | 5 | 6 | 2 |
| 70 | 5 | 5 | 7 | 3 |
| 80 | 6 | 6 | 7 | 4 |
| 90 | 7 | 7 | 8 | 4 |
| 100 | 8 | 8 | 9 | 5 |

TABLE IV-continued

| | Oven test | | | |
|---|---|---|---|---|
| Time (min) | 15% monobutyltin (EGdTG)$_{3/2}$ | 15% monobutyltin $\overset{O}{\underset{\|}{}}$ (SCH$_2$COCH$_2$CH$_2$OC$_4$H$_9$)$_3$ | std. | Example III |
| 110 | 9 | 9 | | 5 |

The results mentioned in the above tables clearly show that at equal concentration the product of Example III displays a far better stabilizing efficiency than similar products known from the art of polymer stabilization.

EXAMPLE VII

In the same PVC formulation as in Example V the following products were subjected to an oven test at 185° C.: BuSn(EGdTG)$_{3/2}$,

BuSn(SCH$_2$COCH$_2$CH$_2$OC$_4$H$_9$)$_3$, and the product of Example IV. The results are given in the following table.

TABLE V

| | Colour development during oven test at 185° C. Time (min) | | | | | | | |
|---|---|---|---|---|---|---|---|---|
| Organotin compound | 0 | 10 | 20 | 30 | 40 | 50 | 60 | 30 |
| BuSn(EGdTG)$_{3/2}$ | 3 | 3 | 4 | 5 | 6 | 9 | 9 | |
| BuSn— $\overset{O}{\underset{\|}{}}$ (SCH$_2$COCH$_2$CH$_2$OC$_4$H$_9$)$_3$ | 3 | 3 | 3 | 4 | 5 | 7 | 9 | 9 |
| Product of ex. IV | 1 | 2 | 2 | 2 | 3 | 4 | 9 | |

The above table clearly demonstrates that for the first fifty minutes the colour development of the PVC with the product of the invention was much slower than similar products that had not been prepared in accordance with the present invention.

EXAMPLE VIII

The effect was determined of a decrease in concentration of the product of Example I. The result is compared with the standard organotin composition known from the art of polymer stabilization.

The PVC formulation used was composed as follows:

| | parts by weight |
|---|---|
| PVC (prepared by suspension polymerization; K-value 60) | 100 |
| glycerol mono oleate | 0,9 |
| external lubricant | 0,6 |
| impact modifier | 5,0 |
| acrylate process aid | 1,0 |

The results of the Mill test are given in the table below.

TABLE VI

| Organotin compound (in parts per 100 parts of resin) | Colour development during Mill test at 185° C. Time (min) | | | | | | | |
|---|---|---|---|---|---|---|---|---|
| | 5 | 8 | 11 | 14 | 17 | 20 | 23 | 26 |
| standard 1,2 phr | 1 | 1 | 3 | 4 | 5 | 6 | 7 stuck | |
| product of ex. I, 1,2 phr | 1 | 1 | 2 | 2 | 3 | 3 | 4 | 7 |
| product of ex. I, 1,08 phr | 1 | 1 | 2 | 2 | 3 | 4 | 4 | 8 |
| product of ex. I, 1,02 phr | 2 | 2 | 2 | 3 | 4 | 4 | 8 | |

The above results clearly show that for the resin composition according to the invention to display the same stabilizing efficiency as in the case of the standard stabilizer, the amount of the product of Example I (according to the invention) to be incorporated into the resin composition was only 90% of that of the standard stabilizer.

EXAMPLE IX

The effect of a reduced concentration of the product of Example VIII was determined on a similar PVC formulation as used in Example III.

The results of the Mill test are given in the table below.

TABLE VII

| Organotin compound (in parts per 100 parts of resin) | Colour development during oven test at 185° C. Time (min) | | | | | | | | | |
|---|---|---|---|---|---|---|---|---|---|---|
| | 5 | 8 | 11 | 14 | 17 | 20 | 23 | 26 | 29 | 32 |
| standard 1,2 phr | 2 | 2 | 3 | 4 | 5 | 6 | 7 | stuck | | |
| product of ex. III, 1,2 phr | 2 | 2 | 2 | 2 | 2 | 2 | 2 | 2 | 3 | 4 |
| product of ex. III, 0,8 phr | 2 | 2 | 2 | 2 | 3 | 3 | 4 | stuck | | |

The above table clearly demonstrates that reduction of the concentration of Example III by more than 30% leads to an even better stabilizing effect than obtained with the use of the generally employed standard organotin composition.

EXAMPLE X

The following PVC formulation was prepared and tested in the above-described way

| | parts by weight |
|---|---|
| PVC (prepared by suspension polymerization K-value 60) | 100 |
| lignite wax, marketed by Hoechst under the trade mark "wax E" | 0,2 |
| acrylate process aid | 2,0 |
| glycerol mono oleate | 1,0 |
| impact modifier | 7,0 |
| stabilizer | 1,0 |

The above formulation was diluted with an amount of epoxidized soya bean oil such that the amount in which it was added formed 10, 15 or 20% by weight of the composition. Even in the case of 20% dilution the stabilizing effect was found to be better than with the use of the standard formulation without addition of epoxidized soya bean oil. The results of the Mill test are given in the table below.

TABLE IX

| Organotin compound | dilution wt. % | Colour development during Mill test at 185° C. Time (min) | | | | | |
|---|---|---|---|---|---|---|---|
| | | 5 | 8 | 11 | 14 | 17 | 20 |
| standard | 0 | 2 | 3 | 4 | 6 | 7 | 9 |
| product of ex. I | 0 | 1 | 2 | 2 | 3 | 3 | 9 |
| product of ex. I | 10 | 2 | 2 | 3 | 4 | 5 | 9 |
| product of ex. I | 15 | 2 | 2 | 3 | 4 | 6 | 9 |
| product of ex. I | 20 | 3 | 3 | 4 | 5 | 6 | 9 |

I claim:

1. An organotin compound containing at least two tin atoms, characterized in that said compound corresponds to the formula

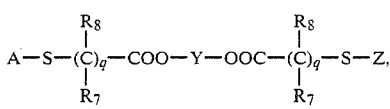

wherein A and Z represent tin-containing organic groups which may be the same or different and both correspond to the formula

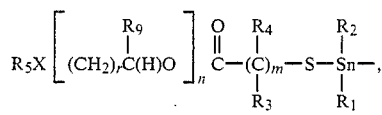

wherein $R_1$ and $R_2$ may be the same or different and may represent an alkyl group having 1 to 18 carbon atoms, the group

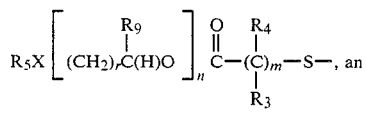

$R_6OCCH_2CH_2$— group or the group

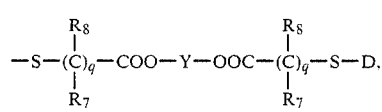

wherein
D corresponds to the same formula as A and Z, provided that in the case where, in the group A, $R_1$ and $R_2$ both represent an alkyl group or the group

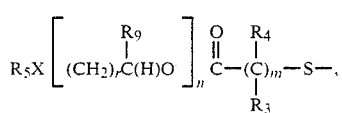

$R_1$ in the group Z and/or D represents an alkyl group and
$R_2$ represents the group

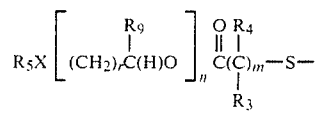

or $R_1$ and/or $R_2$ in the group Z and/or D represent the group

wherein $R_6$ represents an alkyl group having 1 to 18 carbon atoms which may be substituted or not with an alkoxy group having 1 to 18 carbon atoms, a polyoxyalkylene group consisting of oxyalkylene groups having 1 to 4 carbon atoms and of which the end group is an alkyl group or a hydrogen atom, a cycloalkyl group having 3 to 6 carbon atoms, an alkenyl group having 2 to 4 carbon atoms or a phenyl group;

$R_3$, $R_4$, $R_7$ and $R_8$ may be the same or different and have the meaning of a hydrogen atom, an alkyl group having 1 to 18 carbon atoms or an aryl group;

$R_5$ represents a hydrogen atom, an alkyl group having 1 to 18 carbon atoms, a cycloakyl group having 3 to 6 carbon atoms or a substituted or unsubstituted aryl group;

$R_9$ represents a hydrogen atom or a methyl group;

X represents an O or S atom;

Y represents a divalent substituted or unsubstituted aliphatic, cycloaliphatic or aromatic group having not more than 20 carbon atoms; and m and q represent an integer from 1 to 6, n and r an integer from 1 to 3 and p an integer from 1 to 12.

2. An organotin containing compound according to claim 1, characterized in that the groups A, Z and D are identical.

3. An organotin-containing composition according to claim 1, characterized in that the groups

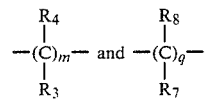

represent a branched or non-branched alkylene group having 1 to 6 carbon atoms, and Y is a branched or non-branched alkylene group or alkylene oxyalkylene group having 2 to 10 carbon atoms.

4. An organotin compound according to claim 1, characterized in that the groups

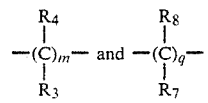

each represent a methylene group or ethylene group, Y is an ethylene group or butylene group, n=1 and $R_5$ an alkyl group having 1 to 8 carbon atoms.

5. An organotin-containing composition for the stabilization of polymers or copolymers of vinyl chloride, comprising at least one organotin compound according to claim 1, wherein $R_1$ represents an alkyl group having 1 to 18 carbon atoms and $R_2$ represents the group

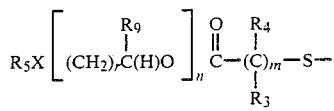

said composition containing a compound of the formula given in claim 15 wherein $R_1$ and $R_2$ may be the same or different and represent an alkyl group having 1 to 18 carbon atoms.

6. An organotin-containing composition according to claim 5, comprising an admixture of said organotin compounds, at least one of said organotin compounds being a monoalkyltin compound and at least one other of said organotin compounds being a dialkyltin compound, said monoalkyltin compound and said dialkyltin compound being present in a weight ratio of at least 1:20.

7. A process according to claim 1, wherein the monofunctional alcohol used is a compound of the formula $R_5X_nH$, wherein the group

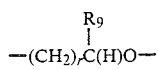

represents a $-CH_2CH_2O-$ or a

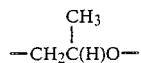

group.

8. A process for the preparation of an organotin compound according to claim 1, in which an organotin oxide or an organotin halide is reacted with the esterification products of a mercapto-substituted carboxylic acid and a monofunctional and a bifunctional alcohol, wherein (A) the organotin compound is an alkyltin compound with a branched or non-branched alkyl group having 1 to 18 carbon atoms or an ester compound wherein $R_1$ and/or $R_2$ in the group Z and/or D represent the group

for the ester group,
(B) the mercapto-substituted carboxylic acid is a compound of the formula

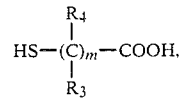

(C) the monofunctional alcohol is a compound which corresponds to the formula $R_5X_nH$,
(D) the bifunctional alcohol is a compound which corresponds to the formula $HO-Y-OH$, and
(E) the molar ratio between the bifunctional alcohol and the monofunctional alcohol is in the range of 1:9 to 9:1.

9. A process according to claim 8, characterized in that the molar ratio between the bifunctional alcohol and the monofunctional alcohol is in the range of 5:9 to 9:1.

10. A process according to claim 8, characterized in that a monoalkyltin compound forms 10 to 20% by weight of the alkyltin compound.

11. Polymers or copolymers of vinyl chloride in which there is incorporated a stabilizing amount of an organotin compound according to claim 1.

12. Polymers or copolymers of vinyl chloride in which there is incorporated from about 0.05 to 3 parts by weight per 100 parts by weight of polymer of an organotin compound according to claim 1, 2, 3 or 4.

13. Shaped articles entirely or partly composed of a polymer or copolymer of vinyl chloride according to claim 11.

* * * * *

UNITED STATES PATENT AND TRADEMARK OFFICE
CERTIFICATE OF CORRECTION

PATENT NO. : 4,546,136

DATED : October 8, 1985

INVENTOR(S) : Boyd COORAY

It is certified that error appears in the above-identified patent and that said Letters Patent is hereby corrected as shown below:

Column 7, line 4, change "choride, compolymers" to --chloride, copolymers--.

Column 11, Table V, line 32, change "30" to --70--.

Column 14, line 41, delete "containing".

Column 15, line 12, change "15" to --1--.

Column 15, line 24, change "1" to --8--.

Column 15, line 26, change "$R_5X_nH$," to $--R_5X\left[(CH_2)_r\overset{R_9}{\underset{|}{C}}(H)O\right]_n H,--$.

Column 16, line 21, change "$R_5X_nH$," to $--R_5X\left[(CH_2)_r\overset{R_9}{\underset{|}{C}}(H)O\right]_n H;--$.

Signed and Sealed this

Eighteenth Day of February 1986

[SEAL]

Attest:

Attesting Officer

DONALD J. QUIGG

Commissioner of Patents and Trademarks